US008455201B2

(12) United States Patent
Hope et al.

(10) Patent No.: US 8,455,201 B2
(45) Date of Patent: Jun. 4, 2013

(54) DIAGNOSE OF MYCOBACTERIAL INFECTIONS BY DETERMINATION OF IFN-GAMMA

(75) Inventors: Jayne Hope, Newbury (GB); Paul Sopp, Newbury (GB); Chris Howard, Newbury (GB)

(73) Assignee: The Pirbright Institute, Pirbright (GB)

( * ) Notice: Subject to any disclaimer, the term of this patent is extended or adjusted under 35 U.S.C. 154(b) by 485 days.

(21) Appl. No.: 12/377,660

(22) PCT Filed: Aug. 14, 2007

(86) PCT No.: PCT/GB2007/003078
§ 371 (c)(1),
(2), (4) Date: Feb. 3, 2010

(87) PCT Pub. No.: WO2008/020185
PCT Pub. Date: Feb. 21, 2008

(65) Prior Publication Data
US 2010/0167319 A1 Jul. 1, 2010

(30) Foreign Application Priority Data

Aug. 15, 2006 (GB) .................................. 0616238.2

(51) Int. Cl.
*G01N 33/53* (2006.01)
(52) U.S. Cl.
USPC ............................ 435/7.1; 435/7.32; 435/7.92
(58) Field of Classification Search
None
See application file for complete search history.

(56) References Cited

U.S. PATENT DOCUMENTS 7,572,597 B2 * 8/2009 Lalvani et al. ................ 435/7.32

FOREIGN PATENT DOCUMENTS

| WO | WO 01/18212 | 3/2001 |
| WO | WO 02/33408 | 4/2002 |
| WO | WO 2004/042396 | 5/2004 |
| WO | WO 2005/118884 | 12/2005 |

OTHER PUBLICATIONS

Buddle et al., "Differentiation between *Mycobacterium bovis* BCG-Vaccinated and *M. bovis*-Infected Cattle by Using Recombinant Mycobacterial Antigens", Clin. Dign. Lab. Immunol., 6:1-5 (1999).
Collins et al., "Bovine interleukin-12 and modulation of IFNγ production", Vet. Immunol. Imunopathol., 68:193-207 (1999).
de la Rua-Domenech et al., "Ante mortem diagnosis of tuberculosis in cattle: A review of the tuberculin tests, γ-interferon assay and other ancillary diagnostic techniques", Research in Veterinary Science, 81:190-210 (2006).
Deveci et al., "Changes in Serum Cytokine Levels in Active Tuberculosis with Treatment", Mediators Inflamm., 5:256-262 (2005).
el-Ahmady et al., "Elevated concentrations of interleukins and leukotriene in response to *Mycobacterium tuberculosis* infection", Ann. Clin. Biochem., 34:160-164 (1997).
Elton et al., "Construction and optimization of an interferon gamma dipstick assay for the detection of antigen-specific cell mediated immune responses" Cornell University, Honors Thesis (May 2007).
Ferraz et al., "A Heterologous DNA Priming-*Mycobacterium bovis* BCG Boosting Immunization Strategy Using Mycobacterial Hsp70, Hsp65, and Apa Antigen Improves Protection against Tuberculosis in Mice", Infection and Immunity, 72:6945-50 (2004).
Garnier et al., "The complete genome sequence of *Mycobacterium bovis*", PNAS, 100:7877-82 (2003).
Gilbert et al., "Cattle movements and bovine tuberculosis in Great Britain", Nature, 435:491-496 (2005).
Hope et al., "NK-like CD8+ cells in immunologically naïve neonatal calves that respond to dendritic cells infected with *Mycobacterium bovis* BCG", J. Leukoc. Biol., 71:184-94 (2002).
Hope et al., "Dendritic Cells Induce CD4+ and CD8+ T-Cell Responses to *Mycobacterium bovis* and *M. avium* Antigens in Bacille Calmette Guérin Vaccinated and Nonvaccinated Cattle", Scand. J. Immunol., 52:285-291 (2000).
Hope et al., "Exposure to *Mycobacterium avium* induces low-level protection from *Mycobacterium bovis* infection but compromises diagnosis of disease in cattle", Clin. Exp. Immunol., 141:432-9 (2005).
Hope et al., "Vaccination of neonatal calves with *Mycobacterium bovis* BCG induces protection against intranasal challenge with virulent *M. bovis*", Clin. Exp. Immunol., 139:48-56 (2005).
Hope and Vordermeier, "Vaccines for bovine tuberculosis: current views and future prospects", Expert Review of Vaccines, 4:891-902 (2005).
Jungersen et al., "Interpretation of the Gamma Interferon Test for Diagnosis of Subclinical Paratuberculosis in Cattle", Clin. Diagn. Lab. Immun., 9:453-460 (2002).
Koets et al., "Mycobacterial 70 kD heat-shock protein is an effective subunit vaccine against bovine paratuberculosis", Vaccine, 24:2550-2559 (2006).
Krebs, "Animal health and welfare. Report by the Independent Scientific Review Group on TB in cattle and badgers", 1997 Review by the Independent Scientific Review Group, led by Professor John Krebs available on http://www.defra.gov.uk.

(Continued)

*Primary Examiner* — Jennifer Graser
(74) *Attorney, Agent, or Firm* — Marshall, Gerstein & Borun LLP

(57) ABSTRACT

The present invention provides a method for diagnosing a mycobacterial infection in a subject, involving the following steps: (i) collection of a sample from the subject; (ii) incubation of the sample from (i) with an antigen preparation for 12 hours or less; and (iii) analysis of γ-IFN in the sample from (ii). The invention also provides a diagnostic kit for use in such a method.

10 Claims, 4 Drawing Sheets

OTHER PUBLICATIONS

Lalvani et al., "Rapid Detection of *Mycobacterium tuberculosis* Infection by Enumeration o Antigen-specific T Cells", Am. J. Respir. Crit. Care Med., 163:824-828 (2001).

Marchant et al., "Newborns Develop a Th1-Type Immune Response to *Mycobacterium bovis* Bacillus Calmette-Guerin Vaccination", J. Immunol., 163:2249-55 (199), 1999.

Mazurek et al., "Guidelines for using QuantiFERON-TB Test for diagnosing Latent *Mycobacterium tuberculosis* Infection", MMWR Recommendations and Reports, 15-18 (2003).

McShane and Hill, "Prime-boost immunisation strategies for tuberculosis", Microbes Infect., 7:962-7 (2005).

McShane et al., "Boosting BCG with MVA85A: the first candidate subunit vaccine for tuberculosis in clinical trials", Tuberculosis, 85:47-52 (2005).

Meade et al., "Gene expression profiling of peripheral blood mononuclear cells (PBMC) from *Mycobacterium bovis* infected cattle after in vitro antigenic stimulation with purified protein derivative of tuberculin (PPD)", Veterinary Immunology and Immunopathology, pp. 1-17 (2006).

Monaghan et al., "The tuberculin test", Vet Microbiol., 40(1-2):111-24 (1994).

Morrison et al., "4.7 Differentiation antigens expressed predominantly on $CD4^-$ $CD8^-$ T lymphocytes (WC1, WC2)", Veterinary Immunology and Immunopathology, 27:71-6 (1991).

Nagabhushanam et al., "Innate Inhibition of Adaptive Immunity: *Mycobacterium tuberculosis*-Induced IL-6 Inhibits Macrophage Responses to IFN-$\gamma^1$", J. Immunol., 171:4750-4757 (2003).

Pollock et al., "The Potential of the ESAT-6 Antigen Secreted by Virulent Mycobacteria for Specific Diagnosis of Tuberculosis", J. Infect. Dis., 175:1251-4 (1997).

Stabel, "Symposium: Biosecurity and Disease. Johne's Disease: A Hidden Threat", J. Dairy Sci., 81:283-288 (1998).

Suni et al. "Detection of antigen-specific T cell cytokine expession in whole blood by flow cytometry", Journal of Immunological Methods, 212:89-98 (1998).

Thom et al., "The effect of tuberculin testing on the development of cell-mediated immune responses during *Mycobacterium bovis* infection", Veterinary Immunology and Immunopathology, 114:25-36 (2006).

van Pinxteren et al., "Diagnosis of Tuberculosis Based on the Two Specific Antigens ESAT-6 and CFP10", Clinical and Diagnostic Laboratory Immunology, 7:155-60 (2000).

Vekemans et al., "Neonatal bacillus Calmette-Guérin vaccination induces adult-like IFN-$\gamma$ production by $CD4^+$ T lymphocytes", Eur. J. Immunol., 31:1531-5 (2001).

Vordermeier et al., "Cellular immune responses induced in cattle by heterologous prime-boost vaccination using recombinant viruses and bacille Calmette-Guérin", Immunology, 112:461-70 (2004).

Vordermeier et al., "Correlation of ESAT-6-Specific Gamma Interferon Production with Pathology in Cattle following *Mycobacterium bovis* BCG Vaccination against Experimental Bovine Tuberculosis", Infection and Immunity, 70:3026-32 (2002).

Weynants et al., "Quantitative assessment by flow cytometry of T-lymphocytes producing antigen-specific $\gamma$-interferon in *Brucella* immune cattle", Veterinary Immunology and Immunopathology, 66:309-320 (1998).

Written Opinion in PCT/GB2007/003078, 2007.

Rothel et al., "The gamma-interferon assay for diagnosis of bovine tuberculosis in cattle: conditions affecting hte production of gamma-interferon in whole blood culture", Australian Veterinary Journal, 69:1-4 (1992).

\* cited by examiner

DIAGNOSE OF MYCOBACTERIAL INFECTIONS BY DETERMINATION OF IFN-GAMMA

This application is the U.S. national phase of International Patent Application No. PCT/GB2007/003078, filed 14 Aug. 2007, incorporated herein by reference, which claims priority benefit of Great Britain Patent Application No. 0616238.2 filed 15 Aug. 2006.

FIELD OF THE INVENTION

The present invention relates to a method for diagnosis of a mycobacterial infection. In particular it relates to a new γ-interferon (γ-IFN) assay, involving analysis of γ-IFN in a subject sample after incubation with antigen. The invention also relates to a kit for use in such a method.

BACKGROUND TO THE INVENTION

Tuberculosis (TB)

The increase in incidence in bovine tuberculosis, caused by infection with *Mycobacterium bovis*, in developed countries such as the UK, New Zealand and the USA, poses significant economic problems and increasing risks to human health. Despite continued use of the skin test and slaughter policy in the UK, the incidence of bovine TB in UK cattle herds is now increasing rapidly. There is now clearly a requirement for improved diagnostic tests and/or vaccination of cattle to halt the spread of this disease and thus reduce economic losses and risks to human health.

Currently, the two most widely used diagnostic tests for tuberculosis in cattle are based on the detection of established cell mediated immune responses: (a) The delayed type hypersensitivity (DTH) response—detected by the comparative tuberculin skin test (Monaghan et al (1994) Vet Microbiol 40(1-2):111-24); (b) the in vitro synthesis of IFN gamma by whole blood cultured with mycobacterial antigens (PPD), that can be subsequently detected by the Bovigam™ ELISA (Hope et al (2005a) Clin. Exp. Immunol. 139:48-56). However, it is well documented that both diagnostic techniques are only partially successful in identifying infected cattle from normal uninfected animals with reported sensitivity ranging from 68 to 95% for the skin test (Monaghan et al (1994, as above).

Incorrect diagnosis may cause significant problems, for example, where false positives exist, the movement restrictions that are placed on farms with herd breakdowns have significant negative economic impact on those affected farms. Infected cattle that are 'missed' by the skin test (false negatives) are a possible source for cattle to cattle transmission of *M. bovis*.

In addition these tests are expensive and time consuming, with a minimum of 2 days from initial sampling to diagnosis by ELISA and 3 days by skin testing. There is thus a need for a new, more rapid, test for TB, preferably one which would allow "same day" diagnosis of infected animals.

To date there are no commercial vaccines available for tuberculosis in cattle. The human vaccine strain BCG produces significant protection, particularly in neonates (Hope et al (2005a) as above), but has been shown to have variably efficacy in cattle, as in humans. More recently, alternative vaccination strategies such as neonatal vaccination (Hope et al (2005a) as above; Marchant et al (199) J. Immunol 163: 2249-55; Vekemans et al (2001) 31:1531-5) and heterologous prime-boost vaccination (Vordermeier et al (2004) Immunology 112:461-70; McShane et al (2005) Tuberculosis 85:47-52; McShane and Hill (2005) Microbes Infect 7:962-7; and Ferraz et al (2004) 72:6945-50), have significantly improved the efficacy of BCG such that it is now being considered for additional trials in humans and cattle (Hope and Vordermeier (2005) Expert Review of Vaccines 4:891-902).

BCG vaccinated individuals test positive by both the skin test and the standard IFNγ test. Differential diagnosis of BCG vaccinated from *M. bovis* infected cattle has been achieved through the use of antigens such as ESAT-6 and CFP-10 (van Pinxteren et al (2000) 7:155-60) present in virulent *M. bovis* but absent from BCG. Reactivity to ESAT-6 and/or CFP10 was shown to correlate with disease severity and could be used to distinguish protected BCG vaccinates from *M. bovis* infected animals (Vordermeier et al (2002) 70:3026-32; Buddle et al (1999) Clin Dign Lab Immunol. 6:1-5). However, reactivity to these antigens is not observed in all *M. bovis* infected animals (Pollock et al (1997) J. Infect Dis 175:1251-4) and is significantly affected by prior sensitisation of cattle to environmental mycobacteria (Hope et al (2005b) Clin Exp Immnnol 141:432-9). Thus, more specific antigens, or more sensitive assay systems are required for accurate diagnosis of bovine TB and distinction of vaccinated individuals.

If BCG vaccination of cattle becomes more widespread, it will no longer be possible to use these standard skin and IFNγ tests routinely because they are unsuitable for vaccinated or part-vaccinated herds. There is thus a need for a simple, inexpensive diagnostic test which can distinguish vaccinated subjects from those which are infected with virulent mycobacteria.

Paratuberculosis (ParaTB)

Paratuberculosis (paraTB) which is also known as Johne's disease, is a chronic progressive enteric disease of ruminants caused by infection with *Mycobacterium paratuberculosis*. ParaTB is widely distributed internationally in domesticated ruminants such as cattle, sheep, goats, as well as deer, antelope and bison. The clinical disease is characterised by chronic or intermittent diarrhoea, emaciation and death. Although animals with clinical disease are often culled, animals with subclinical paraTB cause significant economic losses because of reduced milk production and poor reproductive performance. In addition, shedding of bacteria in the faeces of these animals poses a risk for spread of the disease (Koets et al (2006), Vaccine 24; 2550-2559; Stabel (1998), J. Dairy Sci. 81; 283-288; and Jungersen et al (2002), Clin. Diagn. Lab. Immun. 9; 453-460).

Vaccination against paraTB is not widely used. Currently available vaccines are considered to have variable efficacy and although they reduce clinical disease, their capacity to limit the frequency of subclinical infection, and thus eliminate infection from populations, is very low. A major disadvantage of vaccination is that these interfere with diagnostic tests for paraTB.

Bacteriologic culture is the most definitive method of para diagnosis but is time consuming and labour intensive. There is thus a need for an improved diagnostic method for paraTB, preferably one which is able to differentiate between vaccinated and infected individuals.

SUMMARY OF ASPECTS OF THE INVENTION

The standard IFN-γ test for TB diagnosis for cattle is performed in vitro in two stages. First, whole blood heparinised samples collected on farm are transported to a laboratory immediately after sampling. Small duplicate aliquots are incubated at 37° C. in the presence of test antigens (typically bovine PPD tuberculin and avian PPD tuberculin) and a nil-antigen negative control. After 16-24 hr of incubation, the plasma supernatants are harvested and, if necessary, stored before proceeding to the second step. In the second stage, the amount of IFN-γ in the plasma is quantified by a sandwich enzyme-linked immunosorbent assay (ELISA) using a commercially available kit, such as the Bovigam™ ELISA (de la Rua-Domenech et al (2006) Research in Veterinary Science. In press).

Typically, the test takes 2-3 clays from initial sampling to diagnosis.

The present inventors have surprisingly found that it is possible to reduce significantly the time for incubation of blood samples with antigen and still produce sufficient IFN-γ for detection. Using the standard assay, the incubation time is typically 24 hr. The present inventors have found that this can be reduced to less than 10 hr, for example to about 4-5 hr without adversely affecting the robustness of the assay.

They have also found that, when a shorter incubation time is used, it is possible to distinguish between vaccinated and infected individuals. This is a significant benefit over the standard test which is not able to discriminate reliably between these two subject groups.

Thus, in a first aspect, the present invention provides a method for diagnosing a mycobacterial infection in a subject, which comprises the following steps:
(i) collection of a sample from the subject;
(ii) incubation of the sample from (i) with an antigen preparation for 10 hours or less; and
(iii) analysis of γ-IFN in the sample from (ii).

The mycobacterial infection may be, for example, infection with *M. tuberculosis* or *M. paratuberculosis*.

The sample may, for example be a blood sample.

The sample is incubated with antigen for less than 10 hours. For example, the sample may be incubated with antigen for between 1 and 9, 2 and 8, 3 and 7 or 4 and 6 hours. The sample may be incubated with antigen for about 4 hours, about 5 hours or between 4 and 5 hours.

In order to perform a "one-day" test, γ-IFN in the sample may be analysed by a rapid test system. The results of the analysis may be available, for example, in less than 6 hours, possibly less than 4, 2 or 1 hours.

γ-IFN in the sample may be analysed using a solid-phase assay, such as a dipstick or lateral flow assay (LFA). This type of test enables results to be obtained within a few minutes of application of the incubated sample. For example, the results may be obtained in less than 10 minutes, possibly 1-2 minutes. Another advantage of this type of test is that the equipment needed (for example, the LFA or dipstick) is relatively inexpensive.

In a second aspect, the present invention provides a one-day kit for diagnosis of a mycobacterial infection in a subject which comprises the following:
(i) an incubation tube containing an antigen-preparation; and
(ii) a test for analysis of the amount of γ-IFN in a sample post-incubation.

The test may be a solid-phase test, such as a lateral flow assay (LFA) or a dipstick.

Thus the present invention provides an improved method for the diagnosis of TB in a subject. The method has several advantages:
(i) it enables the diagnosis of TB infected individuals in a single "on-site" visit compared to the normal delay of 2-3 days using standard procedures;
(ii) this, combined with improved analysis techniques (such as the use of solid phase assays) offers significant cost benefits;
(iii) it enables detection of infected animals following vaccination. The existing "skin test" and γ-IFN tests are compromised after animals are vaccinated; and
(iv) it gives improved sensitivity and is less likely to give false-positives than conventional tests.

DETAILED DESCRIPTION

Mycobacterial Infection

Figure 1:
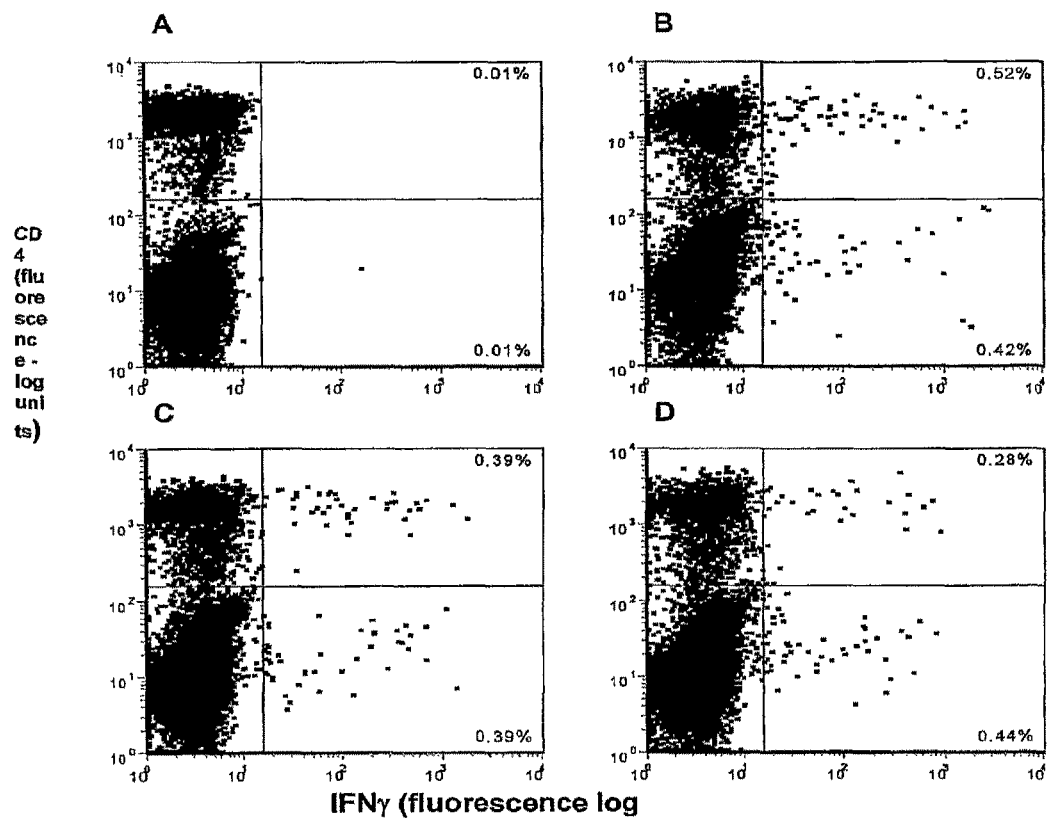
FIG. 1: Detection of intracytoplasmic IFNγ in whole blood cultures Blood taken from *M. bovis* infected animals ten weeks post infection was cultured in vitro for 24 h with PBS (A), PPD-B (B), BCG (C) or *M. bovis* (D). Expression of intracellular IFNγ within $CD4^+$ T cells was examined by flow cytometry. Percentages of cells in each quadrant are illustrated. One representative animal of 3 is shown.

*Mycobacterium* is a genus of *Actinobacteria*, given its own family, the Mycobacteriacaeae. It includes many pathogens known to cause serious diseases in mammals, including tuberculosis and leprosy.

Most mycobacteria share some common characteristics, such as the following:
They are widespread organisms, typically living in water (including tap water treated with chlorine) and food sources.
They can colonize their hosts without the hosts showing any adverse signs. For example, millions of people around the world are unknowingly infected with *M. tuberculosis*.
All mycobacteria are aerobic and acid fast. As a genus, they share a characteristic cell wall, thicker than in many other bacteria, hydrophobic, waxy and rich in mycolic acids/mycolates. The mycobacterial cell wall makes a substantial contribution to the hardiness of this genus.
Mycobacterial infections are notoriously difficult to treat. The organisms are hardy and due to their cell wall, which is neither truly gram negative nor positive and unique to the family, they are naturally resistant to a number of antibiotics that utilize the destruction of cell walls, such as penicillin. Also, because of this cell wall, they can survive long exposure to acids, alkalis, detergents, oxidative bursts, lysis by complement and antibiotics which naturally leads to antibiotic resistance. Most mycobacteria are susceptible to the antibiotics clarithromycin and rifamycin, but antibiotic-resistant strains are known to exist.
Mycobacteria tend to be fastidious (difficult to culture), sometimes taking over two years to develop in culture. As well as being fastidious, some species also have extremely long reproductive cycles (*M. leprae*, for example, may take more than 20 days to proceed through one division cycle; E. coli, for comparison, takes only 20 minutes), making laboratory culture a slow process.

The mycobacterial infection may involve one (or more) of the following species:

M. abscessus, which is also a common water contaminant and was until recently thought to be a subspecies of M. chelonae.

M. africanum

M. asiaticum

Mycobacterium avium complex (MAC), which is a significant cause of death in AIDS patients. This complex also includes M. avium paratuberculosis, which has been implicated in Crohn's disease in humans and Johne's disease in sheep.

M. bovis

M. chelonae, which is a common water contaminant and can also infect wounds.

M. fortuitum

M. gordonae

M. haemophilum

M. intracellulare

M. kansasii, which can cause life-threatening infections in people with compromised immune systems M. lentiflavum M. leprae, which causes leprosy M. malmoense M. marinum M. microti M. phlei M. scrofulaceum M. smegmatis M. triplex M. tuberculosis, which causes tuberculosis M. ulcerans, which causes the "Buruli", or "Baimsdale, ulcer"

M. uvium

M. xenopi

M. paratuberculosis

Mycobacteria of the M. tuberculosis complex can cause tuberculosis. These include M. tuberculosis, M. bovis, M. africanum and M. microti.

Paratuberculosis is caused by infection with M. paratuberculosis.

Tuberculosis

"Tuberculosis" (TB) is a clinical or pathological diagnosis that, by convention, refer to the clinical signs (or lesions) caused by infection with bacteria of the to Mycobacterium tuberculosis (MTB) complex. This is a group of closely related bacteria that includes: Mycobacterium bovis (responsible for TB in cattle and other mammals) and M. tuberculosis (the primary agent of TB in humans).

In humans

During the 19th century, up to 25 percent of deaths in Europe were caused by TB. The death toll began to fall as living standards improved at the start of the 20th century, and from the 1940s, effective medicines were developed. However, there are now more people in the world with TB than there were in 1950, and 3 million individuals every year die from TB.

TB is more common in areas of the world where poverty, malnutrition, poor general health and social disruption are present. However, in some developed countries such as the UK, the number of TB cases is again rising, especially amongst alcoholics, HIV-positive individuals, recent immigrants and healthcare workers.

Syptomatically, tuberculosis is primarily a disease of the lungs. However, the infection can spread via blood from the lungs to all organs in the body. This means that TB can develop in the pleura (the covering of the lungs), in the bones, the ary tract and sexual organs, the intestines and even in the skin. Lymph nodes in the lung root and on the throat can also get infected.

TB is usually transmitted by inhalation of bacteria in the form of microscopic droplets that come from a person with tuberculosis. When coughing, speaking or sneezing, the small droplets are expelled into the air. They dry out quickly, but the bacteria itself can remain airborne for hours. However, the tuberculosis bacteria are killed when exposed to ultraviolet light, including sunlight.

After the tuberculosis bacteria have been inhaled they reach the lungs and, within approximately six weeks, a small primary infection appears that rarely gives any symptoms. The bacteria can then spread through the blood. In healthy individuals the infection can remain dormant for prolonged periods without doing any obvious harm.

Months or even years later, however, the disease can become reactivated in different organs (especially the lungs) if the immune system is weakened.

Typical signs of tuberculosis are: chronic or persistent cough and sputum production. If the disease is at an advanced stage the sputum will contain blood; fatigue; lack of appetite; weight loss; fever; and night sweats.

A rapid TB diagnostic test would be particularly valuable for humans for use in "port of entry" situations. This would enable on-site testing of the infectious state of an individual before entry to a country.

In cattle

Cattle, buffalo and bison are the natural host of M. bovis, but nearly all warm-blooded animals are susceptible to the infection. In fact, compared to other bacteria of the MTB complex, M. bovis has a very broad range of animal hosts. This complicates the control of bovine TB, particularly when the infection becomes self-sustaining in wildlife species, which in turn can become reservoirs of M. bovis for domestic animals.

Bovine TB is spread primarily through the exchange of respiratory secretions between infected and uninfected animals. This transmission usually happens when animals are in close contact with each other. Thus, animal density plays a major factor in the transmission of M. bovis. Bacteria released into the air through coughing and sneezing can spread the disease to uninfected animals.

Bovine TB is a chronic disease and it can take years to develop. M. bovis grows very slowly and only replicates every 12-20 hours. The lymph nodes in the animal's head usually show infection first and as the disease progresses lesions will begin to develop on the surface of the lungs and chest cavity.

Due to the slow progression of infection, the clinical signs of bTB, such as weakness, coughing and loss of weight, are now rarely seen in cattle in countries such at the UK. The Government's compulsory testing and slaughter programme ensures that most cattle herds are tested for bTB at least every four years. This identifies most infected cattle before the disease is apparent.

Cattle to cattle transmission is a serious cause of disease spread (Gilbert, M et al. (2005) Nature 435:491-496). But there is also evidence for a link between bTB in badgers and bTB in cattle (see 1997 Review by the Independent Scientific Review Group, led by Professor John Krebs available on http://www.defra.gov.uk).

Paratuberculosis

Paratuberculosis (paraTB), also known as Johne's disease, is a chronic progressive enteric disease of ruminants caused by infection with *Mycobacterium paratuberculosis*. ParaTB may affect ruminants, particularly domesticated ruminants such as cattle, sheep, goats, as well as deer, antelope and bison. The clinical disease is characterised by chronic or intermittent diarrhoea, emaciation and death. Symptoms of paraTB are similar to those of Chrone's disease in humans.

Subject

The method of the invention may be used to diagnose mycobacterial infection in any susceptible subject.

The subject may be a mammal. The subject may be a wild animal, or an animal in captivity (such as a domestic animal or a zoo animal).

For diagnosis of TB and/or paraTB, the subject may in particular be a domesticated animal such as a cow, buffalo, bison, horse, deer, sheep, pig or goat. Alternatively the subject may be a wild animal which has been associated with the spread of disease. For TB, the following wild animals have been implicated: badgers (in Europe); deer (in America); lions (in Africa) and possums (in New Zealand).

The subject may be a human.

In method where the detection of γ-IFN in the sample is based on an anti-γ-IFN antibody, it may be that the antibody is cross-reactive between species, meaning that the test can be used for a plurality of subject species. For example, the commercially available Bovigam™ kit has been used for the ante-mortem diagnosis of TB in cattle, goats, sheep and African buffalo (de la Rua-Domenech et al (2006) as above).

Sample Collection

γ-IFN is predominantly released by T-lymphocytes after antigenic stimulation. The subject sample may be any body sample which contains T-lymphocytes susceptible to antigenic stimulation. For example, the sample may be a blood sample.

Blood samples may be collected by standard techniques such as venepuncture.

An anti-coagulant may also be added to a blood sample directly after collection, to prevent clotting of the sample. Numerous anti-coagulants are known in the art, including heparin and calcium-binding agents such as EDTA, citrate and oxalate.

The anti-coagulant may, for example, be present in the sample collection tube, optionally along with the antigen preparation.

Antigen Preparation

The antigen preparation may be derivable from a *Mycobacterium*.

For example, for diagnosis of TB infection in cattle, the antigen may be derivable from *Mycobacterium bovis*. For humans, the antigen may be derivable from *M. tuberculosis*. The antigen preparation may be a protein derivative from the *Mycobacterium*. Purified protein derivatives of tuberculin (PPD) are commercially available, such as bovine purified protein derivative of tuberculin (PPD-B).

The antigen preparation may comprise ESAT-6 and/or CFP-10, proteins found in PPD from *M. bovis* but not BCG or other common non-TB mycobacteria. Use of this antigen thus reduces the risk of false positives.

For diagnosis of paraTB infection, the antigen may be derivable from *Mycobacterium paratuberculosis*. The antigen preparation may be or comprise a protein derivative from the *Mycobacterium*, such as PPD-J.

Incubation

The sample may be incubated with the antigen at a temperature between 30-40° C. For example, the incubation temperature may be about 37° C. For "field" use, suitable incubators include portable water baths and heated insulated boxes.

The incubation tube may be adapted to receive the sample directly after collection. For example, the incubation tube may also act as a sample collection tube.

After incubation, a blood sample may optionally be treated to separate the serum. For example, red blood cells may be separated out by brief centrifugation, or by other mechanisms known in the art such as passing the sample through a column which retains the red blood cells or separation using magnetic beads. For field use, a battery-operated centrifuge may be employed. Alternatively, it may be that, during the incubation period, the red blood cells settle sufficiently such that serum can be tested at the top of the tube, without the need for a dedicated separation step.

In the method of the present invention, the sample is incubated with antigen for less than 10 hours. For example, the sample may be incubated with antigen for between 1 and 10, 2 and 9, or 3 and 7 hours. The sample may be incubated with antigen for 4 to 5 or about 4 or about 5 hours.

The incubation time should be long enough to enable sufficient γ-IFN to be produced (by samples from infected individuals) for accurate detection, but short enough to allow "one-day" testing. One-day testing enables diagnosis to be performed at a single site visit. This contrasts with the routinely used skin test which requires two visits from veterinarian: one to perform the test, and one to take the result approximately 72 hours later.

In an embodiment of the invention, the incubation time is chosen such that the method may be used to discriminate between vaccinated and infected individuals.

IFN-γ Analysis

In the method of the first aspect of the invention, IFNγ is analysed in the sample post-incubation with antigen, and optionally post-separation of the serum. The amount of IFNγ may be analysed to give a quantitative measurement, or a relative measurement (for example, when compared to a positive and/or a negative control).

Figure 4:
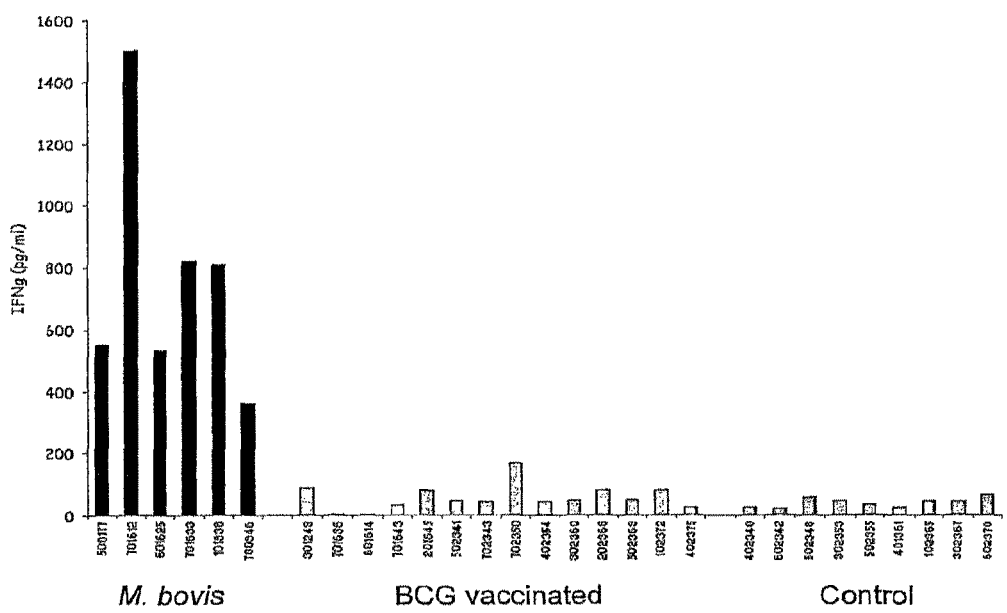
FIG. 4: IFNγ in blood samples from cattle experimentally treated with *M. bovis* (black bars) or non-infected controls (grey bars) after 4 hr incubation.

A diagram summarising possible methodology for the first aspect of the invention, including various IFNγ-analysis techniques is given in FIG. 4.

Elisa/Elispot

In step (iii), γ-IFN in the sample may be analysed using an enzyme-linked immunosorbent assay (ELISA). This may involve removal of an aliquot (maybe 50-100 μl) of the sample post-incubation, for analysis. ELISA sample analysis usually involves determination of γ-IFN against a defined concentration of recombinant γ-IFN (positive control) by their relative optical densities (ODs).

A number of ELISA methodologies, such as those using standard colorimetric or luminescent substrates are known in the art for detection of γ-IFN. For example the Bovigam™ assay is widely used for cattle, and the QuantiFERON™ assay has been developed for humans, non-human primates and cervids, following the development of species-specific monoclonal antibodies against human, primate and cervine γ-IFN (de la Rua-Domenech et al (2006) as above). Numerous other antibodies for the detection of γ-IFN are available (from Serotec™ and others).

ELISPOT is a similar in vitro test that quantifies the number of lymphocytes that produce γ-IFN instead of measuring the total amount of γ-IFN released in response to TB antigens.

A disadvantage of ELISA is that it commonly takes up to 6 hours to perform and uses relatively expensive plate readers that are commonly only found in laboratories.

Also, the ELISA method is dependent on a clear optical path. Cloudy solutions are often not amendable to ELISA conducted in a liquid phase or with the presence of red blood cells or particulate matter.

Fluorescence Polarisation (FP)

It is also possible to use a competitive fluorescence method for analysing γ-IFN in a sample. Fluorescence polarisation (FP) technology is based on the principle that polarised incident visible or UV light that illuminates a fluorochrome causes subsequent polarized fluorescence with emission at a longer wavelength. However, molecules in solution are capable of rotation. Therefore, polarised light striking a fluorescent molecule loses polarisation due to rotation of the molecule. Solutions containing slower turning, large-molecule fluorochrome complexes tends to stay polarized longer verses situations where smaller labelled molecules are present. WO 05/118884 gives more detail on competitive FP methods, including fluorescence lifetime (FLT) and fluorescence resonance energy transfer (FRET).

Two FP readings are necessary: a base-line reading and a reading after a specified time. The FP value increases as the binding of fluorescently labelled ligand occurs. FP technology has the advantage that it can be much more rapid than the 3-4 hours required for an ELISA reading. It is also immune to cloudiness, particles, blood cells (inner filter effects) and does not require a clear optical path. A disadvantage of FP is that it requires sophisticated laboratory equipment for analysis, which does not lend itself to "in the field" testing.

Rapid Test Systems

In order to perform a "one-day" test, γ-IFN in the sample may be analysed by a rapid test system. The results of the analysis may be available, for example, in less than 6 hours, possibly less than 4, 2 or 1 hours. Such systems may also be amenable to testing "on-site" removing the need to transport samples to a laboratory.

For example, γ-IFN in the sample may be analysed using a solid-phase assay, such as a dipstick or lateral flow assay (LFA). This type of test enables results to be obtained within a few minutes of application of the incubated sample. For example, the results may be obtained in less than 10 minutes, possibly 1-2 minutes. Another advantage of this type of test is that the equipment needed (for example, the LFA or dipstick) is relatively inexpensive.

Figure 3:
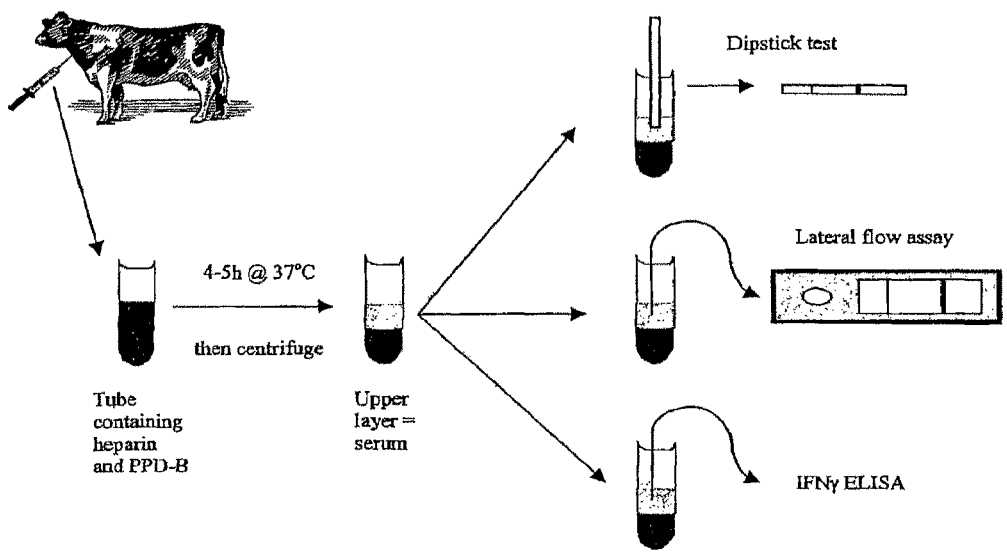
FIG. 3: A schematic diagram illustrating possible methodology for the TB diagnostic test of the invention.

Using a dipstick or LFA, a positive result may be shown as a visual band in the test region (see FIG. 3). This may be compared to a positive control band which develops at the same time (and may be placed "upstream" of the test area in the LFA to ensure that the sample has reached the test area).

The absolute or relative amount of γ-IFN in the sample may be quantitated or compared using an electronic readout system, such as a reflectometer or an ultramicroelectrode inter-digitated array.

Electronic readout systems allow quantitation of the response on a solid phase assay such as a dipstick or LFA. The may also enhance sensitivity compared to reading by eye. In addition, these devices can be directly linked to databases for data management.

Kit

The second aspect of the invention relates to a kit suitable for carrying out the diagnostic method of the first aspect of the invention.

The kit may be a "one-day" kit, meaning that it is capable of providing the diagnostic result within one day of sample collection. The kit may be able to provide a diagnostic result within 12, 10, 8, 6 or 4 hours of sample collection. If a five hour incubation is used together with a rapid test system (such as an LFA or dipstick) the results should be available within about 6 hours of sample collection.

Incubation Tube

The kit includes an incubation tube adapted to receive or containing the antigen preparation. The antigen preparation may be, for example, in liquid or lyophilised form.

The incubation tube may also serve as the sample collection tube, so that the sample is added directly to the antigen preparation.

The incubation/sample collection tube may also contain and anticoagulant such as heparin.

The incubation tube may be adapted for placement in an incubator. For example, it may be shaped to fit in wells of a water bath or insulated box.

The kit may also comprise a means for maintaining the incubation tube at a given temperature (such as 37° C.) such as a portable water bath or a heat insulated box.

The kit also comprises a test for analysis of γ-IFN in a sample post-incubation. The test may be any described above in connection with the first aspect of the invention.

The test may conveniently by a solid-phase test, such as a dipstick or lateral flow assay (LFA).

The kit may also include one or more of the following: instructions for use (detailing the method of the first aspect of the invention); sample collection apparatus (such as a needle and syringe); a chart for interpretation of the results; an electronic readout system; software providing a database for accurate data manan gement.

The kit of the second aspect of the invention may be adapted to measure another parameter in addition to analysis of γ-IFN. The other parameter may also be an indicator of tuberculosis infection, which may be included to increase test sensitivity or accuracy by reducing the number of false positive and/or negative tests.

For example, the kit may include a further test antigen. In the commonly used skin test for bovine TB, PPD-A (avian) is administered intradelinally to one side of the neck of an animal and PPD-B (bovine) is administered to the other side of the neck. Inflammation of the PPD-A injection site (measured using callipers) is indicative of "environmental" (non-specific) reaction, and less significance is given to a reaction to PPD-B in the same animal.

A similar approach could be used in the kit of the present invention. Another antigen (such as PPD-A) could be included to test for a non-specific reaction to the test antigen. Alternatively or in addition, another antigen could be included to test for a second infection. For example, PPD-B and PPD-J could be used to test for infections to diagnose TB and paraTB simultaneously.

Another example would be to test for a further indicator of infection. This could be used to corroborate the test kit result of provide more information about the stage and/or type of infection. For example, IL-10 and IL-6 have been suggested as being indicative of TB infection at different stages. IL-6 has been shown to be elevated in the serum of patients with chronic TB (el-Ahmady et al (1997) Ann Clin Biochem 34:16-164; and Nagabhushanam et al (2003) J. Immunol. 171:4750-4757). IL-10 levels are highest in active TB and that they are reduced as TB is cleared by treatment (Deveci et al (2005) Mediators Inflamm. 5: 256-262). Thus testing for an IFNγ response could be conducted in parallel with assays for other cytokines, such as IL-6 and/or IL-10.

Various examples of such multiplex technology are known in the art. For example, the solid phase test may be a multiplex LFA.

The invention will now be further described by way of Examples, which are meant to serve to assist one of ordinary skill in the art in carrying out the invention and are not intended in any way to limit the scope of the invention.

EXAMPLES

Materials and Methods
Inoculation of Animals with BCG or *M. bovis*

Cattle were British Holstein-Friesian calves (Bos taurus) bred at the Institute for Animal Health. The IAH herd has been confirmed free from bovine TB for more than ten years. Animals were aged 1-12 months at time zero.

Calf groups were (a) non-inoculated control animals; (b) inoculated subcutaneously with $1\times10^6$ cfu BCG Pasteur as previously described (Hope et al (2005a) as above); (c) calves inoculated intranasally with $1\times10^4$ cfu virulent *M. bovis* AF2122/97 ((Hope et al (2005a) as above); experiment 1); (d) calves inoculated intratracheally with $5\times10^3$ *M. bovis* (Vordemeier et al (2002) as above; experiment 2). The control and immunised animals were housed separately in standard animal accommodation and the infected animals were kept in high security (ACDP3) units. The experiments were approved by the local ethics committee according to national UK guidelines.

Antigens and Mycobacteria

Purified protein derivative from *M. bovis* (PPD-B) was obtained from the Tuberculin production unit at Veterinary Laboratories Agency (VLA), Weybridge. BCG Pasteur was diluted from previously titrated frozen (−70° C.) stock grown in Middlebrook 7H9 broth containing 10% ADC supplement (Hope et al (2000) 52: 285-291). Numbers of colony forming units (cfu) were determined on 7H10 agar plates. *M. bovis* strain AF 2122/97 (Gamier et al (2003) PNAS 100:7877-82) grown in 7H9 broth for 7 days was frozen at −70° C. A 1 ml aliquot was thawed and cultured in 10 ml of 7H9 broth for 7 days at 37° C. to produce log phase cells. The $OD_{600}$ was measured and the culture was diluted in 7H9 broth to give an estimated $5\times10^3$ cfu per ml based on a comparison with a previously established standard curve. The number of cfu was determined on 7H11 agar containing 10% OADC supplement and 4.16 g pyruvate per liter.

Collection of Blood

Blood samples were taken by venepuncture at the indicated times post vaccination or challenge. Sodium heparin (Leo Laboratories, Princes Risborough, UK; 10 units per ml) was used as an anti-coagulant. Cultures were set up within 2 h of collection.

Cytokine Flow Cytometry (CFC)

The protocol employed was a modification of that described previously by Suni et al (Suni et al. (1998) 212:89-98). Whole blood samples were incubated for 20-24 hours (or for 5 hours, to test the effect of shorter incubations) at 37° C. with $2.5\times10^5$ cfu *M. bovis*, $2.5\times10^6$ BCG cfu per ml of blood, 20 µg/ml PPD-B or an appropriate volume of PBS as control. The number of cfu of BCG and *M. bovis* added per ml blood was calculated to give cfu/cell ratios of approximately 10:1 and 1:1 respectively. For the final 4 hours of the incubation period 10 µg/ml BFA was added. Following this, RBC were lysed for 30 min with FACSlyse solution (Becton Dickinson, San Jose, Calif., USA; 1 volume 10×FACSlyse mixed with 8 volumes water and added to 1 volume blood). Following two washes in PBS the cells were permeabilised for 20 minin FACS Permeabilizing solution™ (Becton Dickinson, 1 ml per 1 ml blood). After a further two washes in PBS cells were resuspended in PBS/1% BSA/0.1% sodium azide. Aliquots of the cell suspensions were transferred to microtitre plates and stained using a standard indirect immunofluorescence protocol. The following mouse anti-bovine mAbs were used: CD4; CC30 (IgG1) or CC8 (IgG2a); CD8; CC63 (IgG2a); WC1 (Morrison et al (1991) 27:71-6)), CC39 (IgG1) or CC15 (IgG2a): IFNγ; CC302 (IgG1, Serotec, Kidlington, UK), CC302-FITC (Serotec) or 6H5 [IgG2a,(Weynants et al (1998) 66:309-320)]. In some instances mAb were directly coupled to allophycocyanin (APC) using a Phycolink APC conjugation kit (ProZyme, San Leandro, Calif.).

Isotype and concentration matched controls were mouse anti-avian mAb as previously described (Hope et al (2002) J. Leukoc Biol 71:184-94). Where non-conjugated mAbs were used, specific binding was detected with goat anti-mouse IgG1 PE and goat anti-mouse IgG2a FITC (Southern Biotech). The cells were assayed using a flow cytometer (FACSCalibur, Becton Dickinson) and the data were analysed using FCS Express (De Novo Software, Ontario, Canada) The mononuclear cells were identified by light scattering properties and the percentages of CD4, CD8 or WC1 cells that produced IFNγ were calculated.

Example 1

Detection of Intracytoplasmic IFNγ in Response to *M. bovis*, BCG and PPD-B

Blood from *M. bovis* infected animals was cultured for 24 h with *M. bovis*, BCG or PPD-B and the expression of IFNγ within CD4+ T cells was examined (FIG. 1). Each of these antigens stimulated significant increases in IFNγ expressing cells compared to control (FIG. 1a). The in vitro responses to PPD (FIG. 1b), BCG (FIG. 1c) and *M. bovis* (FIG. 1d) varied slightly in terms of the number of responsive cells and the intensity of staining. For further studies PPD-B and BCG were utilised in preference to *M. bovis* to minimise handling of virulent mycobacteria. We also reasoned that a routine diagnostic test requiring the use of *M. bovis* would be impracticable.

Example 2

Figure 2:
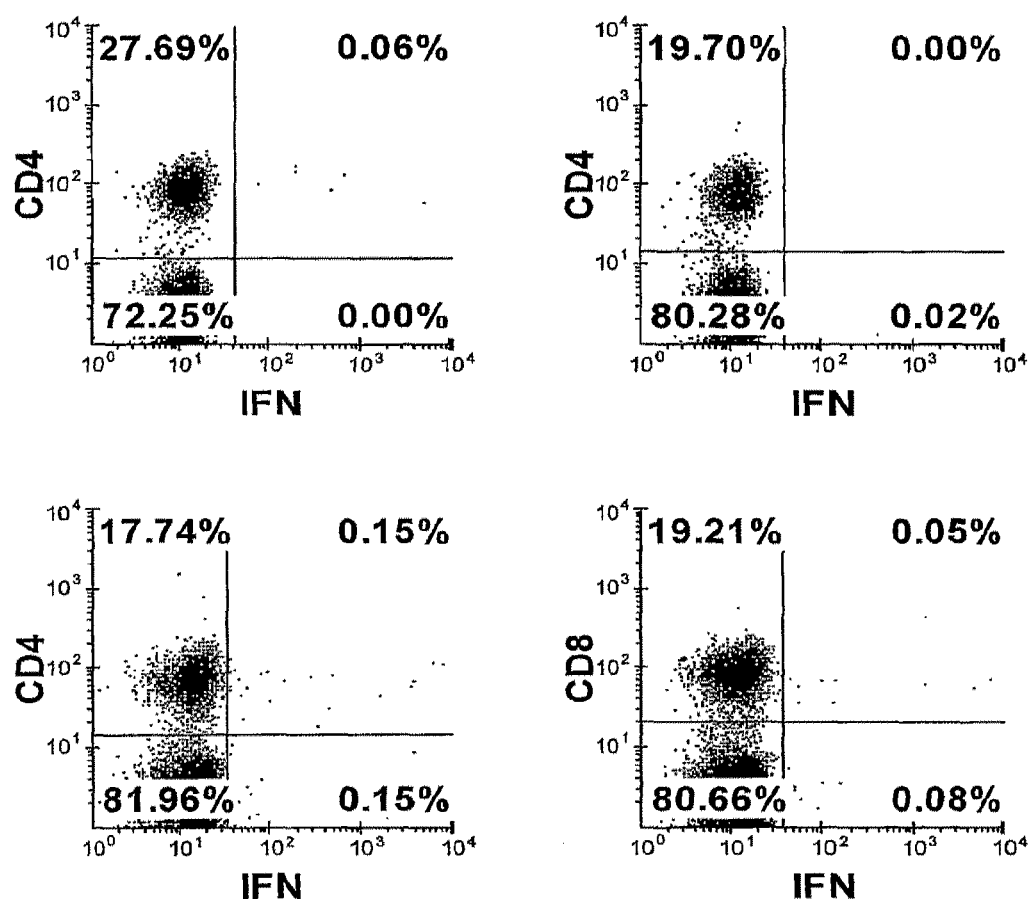
FIG. 2: Detection of intracytoplasmic IFNγ after stimulation for 5 h and 24 h Blood taken from *M. bovis* infected animals ten weeks post infection was cultured in vitro for either 5 h (A, B) or 24 h (C) with PPD-B (A) or BCG (B,C). Expression of intracellular IFNγ within $CD4^+$ T cells was examined by flow cytometry. Quadrants were set based on negative control staining (data not presented). Percentages of cells in each quadrant are illustrated. One representative animal of 3 is shown.

Detection of Intracytoplasmic IFNγ after a Short Incubation in vitro with PPD-B or BCG Whole blood samples from 3 infected animals were incubated with PPD and BCG for 5 and 24 hours to compare responses. Representative results are shown in FIG. 2. Following a 5 h incubation period CD4+ cells expressing IFNγ in response to PPD-B stimulation could clearly be detected (FIG. 2a). However, there was little or no IFNγ detected after 5 h stimulation with BCG (FIG. 2b). By 24 h IFNγ expression in response to BCG stimulation was observed (FIG. 2c).

Example 3

Detection of IFNγ by ELISA after 5 Hour Incubation Time Allows Differentiation of Cattle Infected with *M. bovis* from BCG Vaccinates Blood samples from cattle experimentally infected with *M. bovis* or non-infected controls were taken by venepuncture into tubes containing heparin and PPD. After incubation at 37° C. for 4 hours, samples were centrifuged briefly to separate serum from the red blood cell layer. Aliquots of sera (50-100 µl) were taken and analysed by ELISA using the method described in Collins et al (1999) (Vet Immunol. Immunopathol. 68: 193-207). The results are shown in FIG. 4. The correlation between IFNγ secretion and extent of disease was very high ($r^2$=0.86).

The same experiment was repeated with calves vaccinated with BCG (FIG. 4, central group). The results show that following a 4 hour incubation time, IFNγ can accurately discriminate vaccinated from infected cattle.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A method for detecting *M. bovis* infection in a subject, which comprises the following steps:
   (i) collection of a whole blood sample from an animal;
   (ii) incubation of the sample from (i) with an *M. bovis*, BCG or PPD antigen preparation for between 3 and 6 hours; and
   (iii) detection of gamma interferon (γ-IFN) response in the sample from (ii) whereby detection indicates the presence of *M. bovis* infection.

2. The method according to claim 1, wherein in step (ii), the incubation time is between 4 and 5 hours.

3. The method according to claim 1, wherein in step (iii), γ-IFN in the sample is analysed by a rapid test system.

4. The method according to claim 3, wherein γ-IFN in the sample is analysed using a dipstick or lateral flow assay (LFA).

5. The method according to claim 1, wherein in step (iii), γ-IFN in the sample is analysed using an enzyme-linked immunosorbent assay (ELISA).

6. The method according to claim 1, wherein in step (iii), γ-IFN in the sample is analysed using Fluorescence Polarisation (FP).

7. The method according to claim 1, wherein in step (iii), γ-IFN in the sample is quantitated or compared using an electronic readout system.

8. The method according to claim 7, wherein the electronic readout system is a reflectometer.

9. The method according to claim 7, wherein the electronic readout system is or comprises an ultramicroelectrode interdigitated array.

10. The method according to claim 1, wherein the subject is selected from the group consisting of: cow, badger, human, horse, sheep, pig and goat.

* * * * *

UNITED STATES PATENT AND TRADEMARK OFFICE
CERTIFICATE OF CORRECTION

PATENT NO.        : 8,455,201 B2
APPLICATION NO. : 12/377660
DATED             : June 4, 2013
INVENTOR(S)       : Hope et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 934 days.

Signed and Sealed this

Eighth Day of September, 2015

Michelle K. Lee
*Director of the United States Patent and Trademark Office*